United States Patent
Rispoli et al.

(10) Patent No.: US 7,977,085 B2
(45) Date of Patent: Jul. 12, 2011

(54) PROCESS FOR THE CULTIVATION OF MICRO-ALGAE

(75) Inventors: Giacomo Rispoli, Rome (IT); Emiliano Fioravanti, Rome (IT); Federico Capuano, Rieti (IT); Ezio Nicola D'Addario, Monterotondo (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 12/666,650

(22) PCT Filed: Jun. 17, 2008

(86) PCT No.: PCT/EP2008/005206
§ 371 (c)(1),
(2), (4) Date: Apr. 29, 2010

(87) PCT Pub. No.: WO2009/000534
PCT Pub. Date: Dec. 31, 2008

(65) Prior Publication Data
US 2010/0203618 A1 Aug. 12, 2010

(30) Foreign Application Priority Data

Jun. 26, 2007 (IT) .............................. MI2007A1278

(51) Int. Cl.
*C12N 1/12* (2006.01)

(52) U.S. Cl. .................................. 435/257.1; 435/257.3
(58) Field of Classification Search ............... 435/257.3, 435/257.1
See application file for complete search history.

(56) References Cited

FOREIGN PATENT DOCUMENTS

| | | |
|---|---|---|
| JP | 2008 43321 | 2/2008 |
| WO | 2007 134294 | 11/2007 |

OTHER PUBLICATIONS

Munoz, Raul et al., "Algal-bacterial processes for the treatment of hazardous contaminants: A review", Water Research, Elsevier, vol. 40, No. 15, pp. 2799-2815, (Aug. 1, 2006).
Tam, N. F. Y. et al., "Wastewater Nutrient Removal by Chlorella pyrenoidosa and Scenedesmus sp", Environment Pollution, vol. 58, No. 1, pp. 19-34, (1989).

*Primary Examiner* — Tekchand Saidha
(74) *Attorney, Agent, or Firm* — Oblon, Spivak, McClelland, Maier & Neustadt, L.L.P.

(57) ABSTRACT

Process for the cultivation of micro-algae comprising the planting of an algal strain in an aqueous environment and the growth process, under solar irradiation, by continuously feeding a gaseous stream essentially consisting of carbon dioxide and a stream of nutrients based on nitrogen, consisting of wastewater from industrial plants, coming from secondary treatment processes.

10 Claims, No Drawings

PROCESS FOR THE CULTIVATION OF MICRO-ALGAE

The present invention relates to a process for the cultivation of micro-algae.

More specifically, the present invention relates to a process for the cultivation of micro-algae suitable for being used in the production of biomasses.

Even more specifically, the present invention relates to a process for the cultivation of micro-algae fed with industrial water coming from oil plants, for example refineries.

Studies for the cultivation of algae and micro-algae are known, see, for example, W. J. Oswald, "Journal of Applied Phycology" 15, 99-106, 2003. Micro-algae cultivations generally use fresh or salt water with the addition of nutrients and mineral salts and, when necessary, vitamins, and are effected in open basins having large dimensions, for example from 10 to 100 m long and from 3 to 30 m wide, with a depth of 0.2 to 0.5 m, under solar irradiation. In addition to water, carbon dioxide is fed to the basins, stored, in liquid or gaseous form, in specific tanks, or obtained from the exhausted gases of industrial processing, for example from methane electric power stations, possibly diluted with air. The gaseous phase is bubbled through the liquid mass, through perforated ducts immersed in the growth basin, in order to have the maximum availability of $CO_2$ for the micro-alga.

The cultivation of micro-algae requires few essential components consisting of salts and substances based on nitrogen and phosphorous, in addition to light and $CO_2$ as mentioned above. The minimum nutritional demands can be established on the basis of the following empirical formula of the algal biomass:

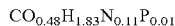

$$CO_{0.48}H_{1.83}N_{0.11}P_{0.01}$$

The algal cultures consequently need P and N in optimal amounts to grow at the necessary rate for maintaining high biomass concentrations. This principle can be exploited for the removal of nitrogenated or phosphorated compounds from industrial wastewater, provided the other compounds present in the water do not create toxicity levels which hinder the growth or functionality of the algal cell.

The Applicant has now found, as better described in the enclosed claims, that the use of industrial water of oil plants, in particular refineries, represents a valid source at least of these nitrogenated nutrients. It has in fact been found that the cultivation of micro-algae in laboratory systems is effected with a substantially unchanged productivity with respect to traditional productions which adopt specific aqueous solutions of nitrogenated nutrients, using, for this purpose, wastewater from refineries, for example.

As is known, civil and industrial wastewater undergoes a first screening process which allows the large dimensioned polluting material to be separated, such as wood, plastic, paper, followed by a (primary) treatment which comprises the sedimentation of coarse suspended solids and other solids, followed by a treatment process (secondary) in which there is the biological oxidation of the organic compounds which can be generally quantified by means of BOD (Biological Oxygen Demand) and COD (Chemical Oxygen Demand). At the outflow of these two types of treatment, the water passes to the nutrient elimination phase (nitrogenated and phosphorated compounds, tertiary treatment). Finally, before being discharged, the process can include a finishing treatment (disinfection, etc.), in relation to the final use of the water.

It has been found that some partially purified industrial water coming from the secondary treatment process contains a certain quantity of nitrogen derivatives, generally at concentrations ranging from 0.1 to 0.5 mg/l, optimum for using this water as a source of nitrogenated nutrient for the cultivation of micro-algae and for allowing these to proliferate in this type of water. This result can be considered surprising, as this industrial wastewater contains, in addition to nitrogenated nutrients, other pollutants, such as chlorides, sulphates, heavy metals, hydrocarbons, phenols, etc., not always suitable, and even toxic with respect to many living species.

The nitrogenated nutrients are generally present as $NH_3$ and ammonia derivatives, for example as organic or inorganic ammonium salts.

In most cases, for the alga to grow, it is necessary to integrate the industrial wastewater with phosphorous nutrient, if this is not present in the industrial waste-water. In general, solutions of water-soluble phosphorous salts are fed, such as alkaline or alkaline-earth metal phosphates, for example sodium, potassium, calcium, magnesium phosphates or ammonium phosphates.

At the end of the growth, with the consequent assimilation and removal of the nutrients (nitrogen and phosphorous), the wastewater is separated and can be poured into surface water basins or subjected to finishing, which allows its recycling-reuse.

Two illustrative and non-limiting examples of the present invention are provided hereunder, which demonstrate the growth of two algal species, one of fresh water (*Scenedesmus* sp.) and one of salt water (*Tetraselmis sk.*) on an industrial effluent.

The following experiments refer to the characterization of micro-algal strains in non-conventional culture mediums. More specifically, the culture medium used was wastewater from an industrial waste treatment plant.

The water coming from the waste treatment unit has the following characteristics:

TABLE 1

Industrial wastewater characteristics

| | Analysis method | Characteristics |
|---|---|---|
| COD (mg/l) | IRSA 5110 | 304.8 |
| Total nitrogen (mg/l) | Kjeldhal | 30.47 |
| Ammonia nitrogen (mg/l) | IRSA CNR | 29.3 |
| Nitric nitrogen (mg/l) | Hach | Absent |
| Conductivity (mS/cm) | IRSA 2030 | 9.79 |
| pH ($-\log_{10}[H+]$) | IRSA 2080 | 7.06 |
| Suspended solids (mg/l) | IRSA 2050 | 99 |
| Chlorides ($Cl^-$) (mg/l) | IRSA 4070 Method A | 4928 |
| Sulphates $SO_4^{2-}$) (mg/l) | IRSA 4120 Method B | 1617 |

Tests were carried out in the laboratory to verify the proliferation of algae in this culture medium, using suitable systems for the growth (Roux bottles) consisting of glass containers of three liters each. The stirring of the culture was guaranteed by the gas (mixture of $CO_2$ in air at 2%) flowing inside the bottles. They were also equipped with a cooling system to prevent the culture temperature from exceeding 30° C. Each unit had sensors for the temperature and pH measurement.

The carbon source for the growth of the algae was provided directly by the $CO_2$ which was introduced into the culture medium under pH control.

The radiant energy to allow the culture to fix the carbon by means of the photosynthesis reaction, was provided by an artificial light system (halogen lamp with a JB trade-mark, 100 watt, positioned 50 cm from the Roux bottle), left on for 24 hours a day, with a luminous intensity of 17,000 lux.

EXAMPLE 1

Fresh Water Strain (*Scenedesmus* sp.)

The collection strain *Scenedesmus* sp. was used. The inoculum to be introduced into the culture systems was prepared as follows:
- a sample of mono-algal culture, previously kept at −85° C. in a 10% solution of glycerine, was defrosted leaving it at room temperature and was then subjected to centrifugation to remove the supernatant.
- the cellular paste thus obtained was inoculated into three 250 ml flasks containing 50 ml of solution containing nutrients.
- the culture was grown in an illuminated climatic chamber at a constant temperature of 30° C., in the presence of $CO_2$ 0.5% in air.
- after about one week, the flask reached a concentration of 0.3 g/l, this culture was used as inoculum for three 1 liter flasks, containing 500 ml of solution containing nutrients and placed in a climatic chamber.
- after 2 days the culture had a concentration of 0.5 g/l, this culture formed the inoculum of the 3 liter Roux bottles used in the experimentation.

The inoculum, prepared as described above, is normally used under the literature conditions (1) listed hereunder:
Literature Growth Conditions
Inoculum: 10% by volume in the medium M4N described hereunder:
Culture medium type M4N:
$KNO_3$, 5.0 g/l;
$KH_2PO_4$, 1.25 g/l;
$CaCl_2$, 0.01 g/l;
$FeSO_4.7H_2O$ 0.003 g/l;
$MgSO_4.7H_2O$ 2.5 g/l;
Micro-elements: 1 ml/l of the following solution: $H_3BO_3$ 2.86 g, $MnCl_2.4H_2O$ 1.81 g, $CuSO_4.5H_2O$ 80 mg, $ZnSO_4.7H_2O$ 220 mg, $Na_2MoO_4$ 210 mg, $FeSO_4.7H_2O$ 25 g, EDTA 33.5 g and 1 drop of concentrated $H_2SO_4$ per liter.
Water: drinkable
Operating pH: 7.8

It was found that these conditions can be improved in terms of operating pH and culture medium as shown in the following examples. The variations for the optimized growth conditions are the following:
Reduction in the $KNO_3$ content from 5.0 to 1.5 g/l;
Addition of $K_2HPO_4$ 0.1 g/l;
Reduction in the content of $MgSO_4.7H_2O$ from 2.5 to 1.5 g/l;
Reduction in the operating pH: from 7.8 to 7.0
Gaseous mix flow: 16 liters/hour.

Three culture systems were prepared for the present experimentation, with the following growth conditions:
Test 1 (Standard Condition, Control)
Inoculum: 10% by volume prepared as described above. Optimized culture medium M4N:
$KNO_3$, 1.5 g/l;
$KH_2PO_4$, 1.25 g/l;
$K_2HPO_4$, 0.1 g/l;
$CaCl_2$, 0.01 g/l;
$FeSO_4.7H_2O$ 0.003 g/l;
$MgSO_4.7H_2O$ 1.5 g/l;
Micro-elements: 1 ml/l of the following solution: $H_3BO_3$ 2.86 g, $MnCl_2.4H_2O$ 1.81 g, $CuSO_4.5H_2O$ 80 mg, $ZnSO_4.7H_2O$ 220 mg, $Na_2MoO_4$ 210 mg, $FeSO_4.7H_2O$ 25 g, EDTA 33.5 g and 1 drop of concentrated $H_2SO_4$ per liter.
Water for the preparation of the culture medium: drinkable
Operating pH: 7.0
Gaseous mix flow 16 liters/hour.
Test 2 (Test with Wastewater+Nutrients)
Inoculum: 10% by volume prepared as described above.
Culture medium: water coming from the industrial water treatment plant, downstream of the secondary treatment, with the composition indicated in Table 1;
Operating pH: 7.0
Optimized culture medium M4N:
$KNO_3$, 1.5 g/l;
$KH_2PO_4$, 1.25 g/l;
$K_2HPO_4$, 0.1 g/l;
$CaCl_2$, 0.01 g/l;
$FeSO_4.7H_2O$ 0.003 g/l;
$MgSO_4.7H_2O$ 1.5 g/l;
Micro-elements: 1 ml/l of the following solution: $H_3BO_3$ 2.86 g, $MnCl_2.4H_2O$ 1.81 g, $CuSO_4.5H_2O$ 80 mg, $ZnSO_4.7H_2O$ 220 mg, $Na_2MoO_4$ 210 mg, $FeSO_4.7H_2O$ 25 g, EDTA 33.5 g and 1 drop of concentrated $H_2SO_4$ per liter.
Water for the preparation of the culture medium: industrial (see table 1).
Operating pH: 7.0
Gaseous mix flow 16 liters/hour.
Test 3 (Test with Wastewater, without Nutrients)
Inoculum: 10% by volume prepared as described above.
Culture medium: not obtained from the outside
Operating pH: 7.0
Water for the preparation of the culture medium: industrial (see table 1).
Gaseous mix flow: 16 liters/hour.
Experimentation Results Culture samples of the three test were collected and subjected to optical density measurements by means of a Varian C 900 spectrophotometer in order to be able to follow the trend of the algal growth.

In addition to these measurements, dry weight measurements were also effected to determine the effective concentration reached by the cultures. Table 2 summarizes the results obtained.

TABLE 2

Résumé of experimental results with *Scenedesmus*

| | Time (hours) | | | | |
|---|---|---|---|---|---|
| | 0 | 5 | 20 | 50 | Dry weight after 50 hrs (g/l) |
| Optical density at 750 nm Test 1 (medium standard M4N) | 0.415 | 0.570 | 1.55 | 3.35 | 0.835 |
| Optical density at 750 nm Test 2 (Gela water + M4N) | 0.670 | 0.830 | 1.5 | 2.54 | 0.925 |
| Optical density at 750 nm Test 3 (Gela water as such) | 0.510 | 0.620 | 1.33 | 2.16 | 0.58 |

From these measurements, it can be clearly deduced that both the growth rate and the final concentration of the culture in the medium consisting of industrial waste-water are comparable with the growth and final concentration of the control culture. This consequently demonstrates that the strain used according to the present invention, under the process conditions indicated, can also be cultivated in industrial wastewater with performances in terms of productivity comparable with those obtained using typical laboratory cultivation conditions.

It should be pointed out that when wastewater without nutrients (Roux 3) is used, the growth kinetics are lower with respect to the other two cases examined (Roux 1 and 2).

EXAMPLE 2

Seawater Strain (*Tetraselmis su.*)

The collection strain *Tetraselmis su.* was used. The inoculum to be introduced into the culture systems was prepared as follows:
- a sample of mono-algal culture, previously kept at −85° C. in a 10% solution of glycerine, was defrosted leaving it at room temperature and was then subjected to centrifugation to remove the supernatant.
- the cellular paste thus obtained was inoculated into three 250 ml flasks containing 50 ml of solution containing nutrients.
- the culture was grown in an illuminated climatic chamber at a constant temperature of 30° C., in the presence of $CO_2$ 0.5% in air.
- after about one week, the flask reached a concentration of 0.3 g/l, this culture was used as inoculum for three 1 liter flasks, containing 500 ml of solution containing nutrients and placed in a climatic chamber.
- after 2 days the culture had a concentration of 0.5 g/l, this culture formed the inoculum of the 3 liter growth systems used in the experimentation.

The inoculum, prepared as described above, is normally used under the literature conditions (2) listed hereunder:
Literature Growth Conditions
Inoculum: 10% by volume in the medium F/2 described hereunder:
Culture medium F/2:
$NaNO_3$, 600 mg/l;
$NaH_2PO_4 bH_2O$, 26.5 mg/l;
$FeCl_3.6H_2O$, 6.3 mg/l (1.3 mg Fe);
$Na_2EDTA$, 8.72 mg/l;
Vitamins 0.5 ml of the following solution:
Thiamine-HCl 0.2 g/l;
Biotin 1.0 mg/l;
B12 1.0 mg/l;
Micro-elements: 0.5 ml/l of the following solution:
$CuSO_4.5H_2O$ 19.6 mg/l (0.005 mg/l Cu);
$ZnSO_4.7H_2O$ 44 mg/l (0.01 mg/l Zn);
$CoCl_2.6H_2O$ 20 mg/l (0.005 mg/l Co);
$MnCl_2.4H_2O$ 360 mg/l (0.1 mg/l Mn);
$Na_2MoO_4.2H_2O$ 12.6 mg/l (0.005 mg/l Mo);
Marine salts for seawater (synthetic) 33 g/l;
Operating pH: 7.8
Water for the preparation of the culture medium: drinkable
Three culture systems were prepared for the present experimentation, with the following growth conditions:
Test 1 (Standard Condition, Control)
Inoculum: 10% by volume in the medium F/2 described above.
Culture medium F/2.
Operating pH: 7.8
Gaseous mix flow: 16 liters/hour.
Water for the preparation of the culture medium: drinkable
Test 2 (Test with Wastewater+Nutrients, Roux 2)
Inoculum: 10% by volume in the medium F/2 described above.
Culture medium F/2.
Operating pH: 7.8
Gaseous mix flow 16 liters/hour.
Water for the preparation of the culture medium: industrial (see table 1).
Test 3 (Test with Wastewater, without Nutrients)
Inoculum: 10% by volume in the medium F/2 described above.
Culture medium: not obtained from the outside
Operating pH: 7.8;
Gaseous mix flow: 16 liters/hour.
Water for the preparation of the culture medium: industrial (see table 1).
Experimentation Results Culture samples of the three test were collected and subjected to optical density measurements by means of a Varian C 900 spectrophotometer in order to be able to follow the trend of the algal growth.

In addition to these measurements, dry weight measurements were also effected to determine the effective concentration reached by the cultures. Table 3 summarizes the results obtained.

TABLE 3

Résumé of experimental results with *Tetraselmis*

| | Time (hours) | | | | Dry weight after 50 hrs (g/l) |
|---|---|---|---|---|---|
| | 0 | 5 | 20 | 50 | |
| Optical density at 750 nm Test 1 (medium standard F/2) | 0.310 | 0.460 | 1.32 | 2.85 | 0.761 |
| Optical density at 750 nm Test 2 (Gela water + F/"2) | 0.530 | 0.720 | 1.5 | 2.64 | 0.821 |
| Optical density at 750 nm Test 3 (Gela water as such) | 0.470 | 0.580 | 1.31 | 2.06 | 0.58 |

The same conclusions can also be drawn for the marine strain as for the fresh water strain. The strain has the same proliferation kinetics both in seawater and in the medium consisting of industrial wastewater containing the growth medium F/2. It should be pointed out that, in the case of the medium consisting of wastewater alone (Test 3) the growth kinetics is lower with respect to the other two cases.

The invention claimed is:

1. A process for cultivating micro-algae, the method comprising planting an algal strain in an aqueous environment that consists of industrial wastewater with a salinity of 1 g/l to 28 g/l, and growing, under solar irradiation, by continuously feeding a gaseous stream, essentially consisting of carbon dioxide and a stream of nutrients based on nitrogen, consisting of wastewater from industrial plants, containing it, coming from secondary treatment processes.

2. The process according to claim 1, wherein the algae are selected from chlorophyte algae.

3. The process according to claim 1, wherein the algae are chlorophytes from collection strains selected from *Tetraselmis suecica, Scenedes mus sp, Phaeodactylum tricornutum, Chlorella vulgaris*, or from autochthon strains identified in the proximity of the industrial plant.

4. The process according to claim 1, which further comprises feeding a second aqueous stream of nutrients containing phosphorous salts in solution in a concentration ranging from 0.01 to 0.05 g/l.

5. The process according to claim 1, wherein the gaseous stream contains from 6 to 100% by volume of $CO_2$.

6. A process for cultivating micro-algae, the method comprising
  planting an algal strain in an aqueous environment; and
  growing the algal strain, in the presence of solar irradiation, by continuously feeding a gaseous stream of carbon dioxide and a stream of nitrogen-based nutrients comprised within secondarily treated wastewater from an industrial plant,
  wherein the industrial plant is an oil refinery, wherein the aqueous environment has a salinity of 1 g/l to 28 g/l.

7. The process according to claim 6, wherein the algae are chlorophyte algae.

8. The process according to claim 6, wherein the algae are *Tetraselmis suecica, Scenedesmus* sp, *Phaeodactylum tricornutum, Chlorella vulgaris*, or from an autochthon strain identified in a proximity of the industrial plant.

9. The process according to claim 6, which further comprises feeding a second aqueous stream of nutrients containing phosphorous salts in solution in a concentration ranging from 0.01 to 0.05 g/l.

10. The process according to claim 6, wherein the gaseous stream comprises from 6 to 100% by volume of $CO_2$.

* * * * *